(12) United States Patent
Ishizaki et al.

(10) Patent No.: US 8,722,133 B2
(45) Date of Patent: May 13, 2014

(54) METHOD FOR PRODUCTION OF ORALLY RAPIDLY DISINTEGRATING TABLET COMPRISING IMIDAFENACIN AS ACTIVE INGREDIENT

(75) Inventors: Toshihiro Ishizaki, Shimotsuga-gun (JP); Yoshinobu Aoki, Shimotsuga-gun (JP)

(73) Assignee: Kyorin Pharmaceutical Co., Ltd., Tokyo (JP)

(*) Notice: Subject to any disclaimer, the term of this patent is extended or adjusted under 35 U.S.C. 154(b) by 596 days.

(21) Appl. No.: 12/865,632

(22) PCT Filed: Jan. 30, 2009

(86) PCT No.: PCT/JP2009/051651
§ 371 (c)(1),
(2), (4) Date: Sep. 3, 2010

(87) PCT Pub. No.: WO2009/096559
PCT Pub. Date: Jun. 8, 2009

(65) Prior Publication Data
US 2010/0323090 A1 Dec. 23, 2010

(30) Foreign Application Priority Data
Jan. 31, 2008 (JP) ................................. 2008-020183

(51) Int. Cl.
*A61K 9/20* (2006.01)
*A61K 9/26* (2006.01)
*A61K 9/28* (2006.01)

(52) U.S. Cl.
USPC ........... 427/2.14; 424/464; 424/465; 424/470

(58) Field of Classification Search
USPC ......................................... 424/465; 427/2.14
See application file for complete search history.

(56) References Cited

U.S. PATENT DOCUMENTS

| | | | |
|---|---|---|---|
| 5,932,607 A | 8/1999 | Miyachi et al. | |
| 6,248,357 B1 * | 6/2001 | Ohno et al. | 424/465 |
| 7,229,643 B2 * | 6/2007 | Cochran et al. | 424/480 |
| 7,351,429 B1 * | 4/2008 | Ohyama et al. | 424/465 |
| 2003/0026835 A1 * | 2/2003 | Nishii et al. | 424/465 |
| 2006/0159760 A1 * | 7/2006 | Yoneyama et al. | 424/472 |
| 2006/0188554 A1 | 8/2006 | Nakashima et al. | |
| 2007/0021391 A1 * | 1/2007 | Doi et al. | 514/114 |
| 2007/0092566 A1 | 4/2007 | Hoshino et al. | |
| 2008/0107727 A1 | 5/2008 | Nakashima et al. | |

FOREIGN PATENT DOCUMENTS

| | | |
|---|---|---|
| JP | 7 215943 | 8/1995 |
| JP | 2004 339071 | 12/2004 |
| JP | 2004339071 A * | 12/2004 |
| WO | 00 47233 | 8/2000 |
| WO | 01 34147 | 5/2001 |
| WO | WO 0134147 A1 * | 5/2001 |
| WO | 1 153 616 A1 | 11/2001 |
| WO | 1 245 232 A1 | 10/2002 |
| WO | 2005 011682 | 2/2005 |
| WO | 2005 011683 | 2/2005 |
| WO | 2005 105045 | 11/2005 |
| WO | 2006 080481 | 8/2006 |
| WO | 2006 082888 | 8/2006 |

OTHER PUBLICATIONS

U.S. Appl. No. 12/865,737, filed Aug. 2, 2010, Ishizaki, et al.
Miyachi, H. et al. " Synthesis and Antimuscarinic Activity of a Series of 4-(1-Imidazolyl)-2-2-Diphenylbutyramides: Discovery of Potent and Subtype-Selective Antimuscarinic Agents", Bioorganic & Medicinal Chemistry, vol. 7, pp. 1151-1161 (1999).
European Serach Report issued Jan. 31, 2013 in corresponding European Patent Application No. 09705447.2, 4 pp.

* cited by examiner

*Primary Examiner* — Timothy Meeks
*Assistant Examiner* — Cachet Sellman
(74) *Attorney, Agent, or Firm* — Oblon, Spivak, McClelland, Maier & Neustadt, L.L.P.

(57) ABSTRACT

The present invention herein provides an imidafenacin-containing orally rapidly disintegrating tablet which is excellent in the photostability.
The present invention comprises the steps of: (A) granulating imidafenacin together with starch to thus give a granulated product having an imidafenacin concentration ranging from 0.001 to 3% by mass and a starch concentration ranging from 40 to 99.999% by mass; (B) covering the granulated product prepared in the step (A) with a non-cellulosic coating agent; and (C) blending the granulated product obtained in the preceding step (B) with an excipient and a disintegrating agent and then forming the resulting mixture into a tablet according to the compression molding technique.

20 Claims, No Drawings

METHOD FOR PRODUCTION OF ORALLY RAPIDLY DISINTEGRATING TABLET COMPRISING IMIDAFENACIN AS ACTIVE INGREDIENT

TECHNICAL FIELD

The present invention relates to a method for preparing an orally rapidly disintegrating tablet comprising imidafenacin as an active ingredient.

BACKGROUND ART

Imidafenacin is a compound having an antagonistic action in respect of muscarinic receptors M3 and M1 (see Patent Document 1 specified below), and it is put at service as a medicament for treating overactive bladder (see Non-Patent Document 1 specified below). As pharmaceutical preparations comprising imidafenacin as a main active ingredient, there have been known, for instance, an orally-administered solid pharmaceutical preparation and a transdermal therapeutic system, each of which contains imidafenacin (see Patent Documents 2 and 3 specified below).

More specifically, Patent Document 2 discloses that the imidafenacin-containing pharmaceutical preparation is photosensitive and that the pharmaceutical preparation in the form of a tablet is correspondingly covered with a coating liquid which contains titanium oxide and iron sesquioxide to thus make the tablet photo-stable. However, Patent Document 2 relates to a product prepared by compressing an imidafenacin-containing granulated product into tablet and then applying a coating onto the resulting tablet and this Patent Document does not discloses any orally rapidly disintegrating tablet at all.

In addition, Patent Document 3 relates to a pharmaceutical preparation of the transdermal therapeutic system type and therefore, the pharmaceutical preparation disclosed therein is different from the orally rapidly disintegrating tablet in the dosage form.

Incidentally, Patent Documents 4 and 5 each disclose a method for the preparation of an orally-administered pharmaceutical preparation. However, Patent Documents 4 and 5 relate to a method for the preparation of a pharmaceutical preparation in a sustained release type dosage form. Accordingly, a gel-forming substance is used in the dosage form disclosed in Patent Document 4 and the tablet formed using such a gel-forming substance cannot be a disintegrating one. Moreover, in respect of the pharmaceutical preparation disclosed in Patent Document 5, this document does not disclose that starch, as an excipient, in an amount of not less than 40% by mass is used when granulating imidafenacin to thus considerably improve the photostability of the resulting pharmaceutical preparation.

On the other hand, there have intensively been conducted the development of pharmaceutical preparations while introducing improvements in manufacturing formulations into the development thereof, with the objective of improving the "Quality of Life (QOL)" of a patient. Most frequently or vigorously developed pharmaceutical preparations are orally rapidly disintegrating tablets, among others. The orally rapidly disintegrating tablet can instantaneously be disintegrated in the presence of even a small amount of saliva within the oral cavity and accordingly, the tablet can easily be administered to a patient and may be an optimum pharmaceutical preparation for administering it to elderly peoples and children who cannot swallow the tablets with ease. In addition, the tablet of this type may have such a merit that it can be taken without any help of water and accordingly, there is not any limit in the place and/or time for the administration thereof.

However, it would be quite difficult to apply a coating comprising titanium oxide and iron sesquioxide, to the orally rapidly disintegrating tablet while ensuring the maintenance of the disintegration property of the tablet and accordingly, there has not yet been proposed any report on the orally rapidly disintegrating tablet containing imidafenacin as an effective component.

Non-Patent Document 1: Bioorg. Med. Chem., 1999, Vol. 7, pp. 1151-1161;
Patent Document 1: JP-A-7-215943;
Patent Document 2: WO 01/34147 A1 pamphlet;
Patent Document 3: WO 2006/082888 A1 pamphlet;
Patent Document 4: WO 2005/011682 A1 pamphlet;
Patent Document 5: WO 2006/0808481 A1 pamphlet.

DISCLOSURE OF THE INVENTION

Problems that the Invention is to Solve

It is an object of the present invention to provide a method for the preparation of an orally rapidly disintegrating tablet which contains imidafenacin and which is excellent in the photostability and the uniformity of the content of the active pharmaceutical ingredient.

Means for the Solution of the Problems

The inventors of this invention have conducted intensive studies to solve the foregoing problems and, have found that an intended orally rapidly disintegrating tablet, which is excellent in the photostability and the content uniformity, can effectively be prepared by applying a coating agent onto an imidafenacin-containing granulated product and adjusting the contents of imidafenacin and starch in the granulated product, and have thus completed the present invention.

More specifically, the present invention relates to a method for preparing an orally rapidly disintegrating tablet which comprises the following steps:

(A) granulating imidafenacin together with starch to thus give a granulated product having an imidafenacin concentration ranging from 0.001 to 3% by mass and a starch concentration ranging from 40 to 99.999% by mass;

(B) covering the granulated product prepared in the foregoing step (A) with a non-cellulosic coating agent; and (C) blending the granulated product obtained in the preceding step (B) with an excipient and a disintegrating agent and then forming the resulting mixture into a tablet according to the compression molding technique.

Effects of the Invention

The present invention thus permits the easy preparation of an imidafenacin-containing orally rapidly disintegrating tablet which is excellent in the photostability and the content uniformity.

BEST MODE FOR CARRYING OUT THE INVENTION

Now, the present invention will be described below in more detail.

In the specification of this patent application, the term "orally rapidly disintegrating tablet" means a solid pharmaceutical preparation for medical use, which can disintegrate, within the oral cavity and in the presence of saliva, within a term shorter than about 90 seconds, preferably shorter than about 60 seconds and further preferably shorter than 40 seconds, without any mastication.

Imidafenacin used, as an effective component, in the orally rapidly disintegrating tablet of the present invention is 4-(2-methyl-1-imidazolyl)-2,2-diphenylbutylamide serving as a therapeutic agent for treating a patient suffering from urinary frequency and urinary incontinence, which has an anti-cholinergic effect selective for the bladder. The content of imidafenacin included in the orally rapidly disintegrating tablet preferably ranges from 0.05 to 0.8 mg per tablet and more preferably 0.1 to 0.2 mg per tablet.

According to the method of the present invention, imidafenacin is first granulated together with starch. In this respect, other additives such as an excipient and a binder may be incorporated into the granulated product in combination, as the need arises. In particular, the use of starch as an excipient would permit the impartment of excellent photostability to the resulting granulated product as compared with that observed when using other excipient such as D-mannitol or magnesium metasilicate aluminate.

The amount of imidafenacin to be used ranges from 0.001 to 3% by mass on the basis of the mass of the granulated product. Regarding the lower limit of the amount of imidafenacin, it would be suitable that the amount thereof is preferably not less than 0.005% by mass, more preferably not less than 0.01% by mass, still more preferably not less than 0.05% by mass, still further preferably not less than 0.1% by mass and particularly preferably not less than 0.2% by mass. On the other hand, regarding the upper limit of the amount of imidafenacin, it would be suitable that the amount thereof is preferably not more than 2% by mass, more preferably not more than 1% by mass, still more preferably not more than 0.8% by mass and particularly preferably not more than 0.6% by mass, while taking into consideration the uniformity of content.

Starch is herein used in an amount ranging from 40 to 99.999% by mass, preferably 50 to 99.95% by mass, more preferably 60 to 99.9% by mass and particularly preferably 70 to 99.8% by mass on the basis of the mass of the granulated product. The use of starch in an amount falling within the range specified above would permit the preparation of an orally rapidly disintegrating tablet excellent in the photostability.

As the starch component, suitably used herein is partly pregelatinized one from the viewpoint of its photostability.

Examples of other excipients used, if necessary, simultaneously with the starch component include saccharides such as lactose and glucose, as well as celluloses such as crystalline cellulose. In addition, examples of the foregoing binders include crystalline cellulose, saccharides, dextrin, hydroxypropyl cellulose, Hydroxypropyl Methylcellulose, gum Arabic, gelatine and pullulan.

The imidafenacin-containing granulated product can be prepared according to any granulation technique such as the dry granulation method, the agitation granulation method, the extrusion-granulation method, the fluidized bed-granulation method, the tumbling fluidized bed-granulation method, or the spray drying granulation method. Suitably used herein as such granulation techniques are preferably the fluidized bed-granulation method and the tumbling fluidized bed-granulation method.

The average particle size of the resulting granulated product ranges, for instance, from 0.1 to 350 μm and preferably 50 to 200 μm. Additional components other than the medicinal component, the excipient such as starch and the binder has been described above can further be incorporated, as appropriate, into the granulated product so far as the intended effect of the present invention is not impaired.

In addition, the imidafenacin-containing granulated product may be dried after the formation of the granulated product, from the viewpoint of the stability of the medicinal component used therein and the insurance of the easy forming property of the product into a tablet. The drying method usable herein is not restricted to any particular one inasmuch as it can be used in the production of medicinal preparations.

The imidafenacin-containing granulated product is further covered with a non-cellulosic coating agent in order to make the same photo-stable. Such a non-cellulosic coating agent usable herein may be, for instance, a water-soluble coating agent, a hydrophobic coating agent or a gastric juice-soluble coating agent, or further an enteric coating agent.

As the water-soluble coating agents, suitably used herein include, for instance, pH-independent coating agents such as povidone.

In addition, examples of hydrophobic coating agents suitably used herein are stearyl alcohol and ammonio-methacrylate copolymers.

Examples of the foregoing gastric juice-soluble coating agents suitably used herein include aminoalkyl methacrylate copolymer E and polyvinyl acetal-diethylamino-acetate.

Examples of the foregoing enteric coating agents suitably used herein include methacrylic acid copolymers (L, S).

The amount of the coating agent to be used for the coating of the granulated product is not restricted to any specific one, but it preferably ranges from about 0.001 to 10 parts by mass, more preferably about 0.01 to 1 part by mass and particularly preferably about 0.05 to 0.5 parts by mass per one part by mass of the granulated product. In this respect, the method for applying the coating agent to the granulated product is not restricted to any specific one insofar as it can be used in the production of medicinal preparations. For instance, suitably used herein are the spray coating method, the dip coating method and the hot melt-coating method.

Incidentally, a lubricant such as magnesium stearate may be incorporated into the coating agent, if necessary.

The orally rapidly disintegrating tablet according to the present invention can be produced by incorporating an excipient and a disintegrating agent into the imidafenacin-containing granulated product and then subjecting the resulting blend to the compression molding operation.

As has been discussed above, the excipient herein incorporated into the granulated product is not limited to any specific one, inasmuch as it can be used in the production of medicinal preparations and examples thereof usable herein are those disclosed in Dictionary of Drug Additives, edited by The Association of Drug Additives in Japan, published by YAKUJI-NIPPO Publishing Company (2007). Specific examples thereof include saccharides such as lactose and glucose, sugar alcohols such as D-sorbitol and mannitol, celluloses such as crystalline cellulose, and starches such as partly pregelatinized starch and corn starch. Preferably used herein are sugar alcohols among others.

The foregoing disintegrating agent to be blended with the granulated product is not likewise limited to any specific one inasmuch as it can be used in the production of medicinal preparations and examples thereof usable herein, as appropriate, are those disclosed in Dictionary of Drug Additives, edited by The Association of Drug Additives in Japan, published by YAKUJI-NIPPO Publishing Company (2007). Specific examples thereof include celluloses such as calcium carboxymethyl cellulose, hydroxypropyl cellulose having a low degree of substitution, croscarmellose sodium and methyl cellulose, crospovidone, with crospovidone being preferably used herein because of its immediate disintegration property and the easiness of swallowing the resulting tablet (agreeableness to the palate).

The amount of the excipient and disintegrating agent to be suitably incorporated with the granulated product into the orally rapid disintegrating tablet falls within the range of, for instance, from 1 to 50 parts by mass and preferably 3 to 25 parts by mass per one part by mass of the coated imidafenacin-containing granulated product.

In the present invention, when blending the excipient and the disintegrating agent with the coated and granulated product, any additive usable in the production of medicinal preparations can be incorporated, as appropriate, into the tablet, if necessary. Such additives usable in the present invention include, for instance, those disclosed in Dictionary of Drug Additives, edited by The Association of Drug Additives in Japan, published by YAKUJI-NIPPO Publishing Company (2007). Specific examples thereof suitably used herein include lubricants such as stearic acid and metal salts thereof, as well as talc, light anhydrous silicic acid, hydrated silicon dioxide and sucrose esters of fatty acids; sweetening agents such as saccharides, sugar alcohols, aspartame, saccharin and salts thereof, glycyrrhizic acid and salts thereof, stevia and acesulfame potassium; corrigents (taste- and/or odor-improving agents) such as citric acid, sodium citrate, succinic acid, tartaric acid and fumaric acid; coloring agents such as iron sesquioxide, yellow iron sesquioxide, caramel, riboflavin and aluminum lakes; and perfumes such as menthol and orange oil extract.

The shape of the tablet formed according to the present invention is not limited to any particular one so far as it never impairs the intended effects of the present invention. For instance, the tablet may be formed into even a specific shape such as an inside-bored shape, a polygonal shape or a concave shape. Moreover, the tablet may likewise be formed into a flat-shaped tablet which is thin and has a large diameter in order to increase the contact area between the tongue and the tablet in the oral cavity to thus make the moisture within the oral cavity immediately penetrate into the interior of the tablet and to thereby improve the orally rapid disintegration property of the tablet.

The blending of the additive components may be carried out according to the usual blending method and the blending may be carried out using, for instance, a device such as a V-shaped blender, a diamond mixer and a drum mixer. Regarding the compression molding, the usual tableting machine may be used. For instance, a rotary tableting machine may be used.

The pressure used in the compression molding falls within the range of, for instance, from 300 to 2,000 kg and preferably 600 to 1,000 kg and the compression molding can be implemented under the conditions of room temperature and 60% RH.

The present invention will hereunder be described in more detail with reference to the following Examples, Comparative Examples and Test Examples.

The following are the description of the methods used for evaluating the imidafenacin-containing granulated product and the coated granules prepared from the same:
[Determination of Particle Size Distribution]: The particle size was determined in a screening type particle size distribution-determining device (ATM; Sonic Shifter Co., Ltd.) while using sieves each having a mesh size of 75, 106, 150, 180, 212 or 355 μm.

In addition, the average particle sizes (50% diameter) thereof were calculated on the basis of the results obtained in the determination of the particle size distribution.

The methods used for the various evaluation of the orally rapidly disintegrating tablet were as follows:
[Hardness Test]: The hardness of the tablet was determined using a tablet hardness meter (Okada Seiko Co., Ltd.). Each test was carried out using 5 tablets and each of the experimental results was the average of 5 measurements.
[Disintegration Test]: The disintegration time of the tablet was determined using a disintegration apparatus (TOYAMA Sangyo Co., Ltd.). Each test was carried out using 6 tablets and each of the experimental results was the average of 6 measurements. Water was used as a test liquid and the time required till each tablet was completely disintegrated and dissolved in water was determined.

Incidentally, the compounds represented by their trade names and used in the following Examples and Comparative Examples were as follows (see, for instance, Dictionary of Drug Additives 2007, published by YAKUJI-NIPPO Publishing Company):
1. Trade Name: Starch 1500G (Colorcon Japan, LLC): Partially pre-gelatinized starch;
2. Trade Names: CEOLUS PH-301 and PH-102 (ASAHIKASEI Chemicals Co., Ltd.): Crystalline celluloses;
3. Trade Name: Kollidon 90F (BASF Japan Ltd.): Povidone;
4. Trade Name: Kollidon 25 (BASF Japan Ltd.): Povidone;
5. Trade Name: EUDRAGIT EPO (Rohm GmbH & Co. KG): Methyl methacrylate-butyl methacrylate-dimethylaminoethyl methacrylate copolymer or aminoalkyl methacrylate copolymer E;
6. Trade Name: EUDRAGIT L100-55 (Rohm GmbH & Co. KG): Dried methacrylic acid copolymer LD;
7. Trade Name: EUDRAGIT RSPO (Rohm GmbH & Co. KG): Ethyl acrylate-methyl methacrylate-chlorotrimethylammonium ethyl methacrylate copolymer or aminoalkyl methacrylate copolymer RS;
8. Trade Name: magnesium stearate (derived from vegetable) (Taihei Chemical Industry Co., Ltd.);
9. Trade Name: PEARLITOL (ROQUETTE JAPAN Co., Ltd.): D-Mannitol;
10. Trade Name: Kollidon CL-F (BASF Japan Ltd.): Crospovidone;
11. Trade Name: polyplasdone XL-10 (ISP Company): Crospovidone;
12. Trade Name: CARPREX #67 (DSL Japan Co., Ltd.): Hydrated silicon dioxide;
13. Trade Name: AEA (Sankyo LifeTech Co., Ltd.): Polyvinyl acetal diethylamino acetate;
14. Trade Name: ETHOCEL 7 Premium (Nissin Chemical Industry Co., Ltd.): Ethyl cellulose;
15. Trade Name: TC-5RW (Shin-Etsu Chemical Co., Ltd.): Hydroxypropyl Methylcellulose.

Example 1

There were dissolved 25.0 g of imidafenacin and 12.5 g of Kollidon 90F (BASF Japan Ltd.) in a mixed liquid comprising 738.75 g of purified water and 1723.75 g of ethanol. Then, there was charged 4962.5 g of Starch 1500G (Colorcon Japan, LLC) into a fluidized bed granulator (FL-5, FREUND Industry Co., Ltd.) and the foregoing solution was then applied to (coated) the starch according to the top-spray technique (amount of liquid to be sprayed: 100 g/min, air pressure used for spray: 0.3 MPa, air supply temperature: 70° C.) to thus give an imidafenacin-containing granulated product (average particle size: 128 μm; starch content: 99.25% by mass). Separately, there were dissolved 750 g of EUDRAGIT EPO (Rohm GmbH & Co. KG) and 375 g of magnesium stearate (derived from vegetable) (Taihei Chemical Industry Co., Ltd.) in a mixed liquid comprising 3412.5 g of purified water and 7962.5 g of ethanol. Then, there was charged 3750 g of the imidafenacin-containing granulated product prepared above into a fluidized bed granulator (FL-5, FREUND Industry Co., Ltd.) and the solution thus prepared was then applied to the granulated product according to the top-spray technique (amount of liquid to be sprayed: 100 g/min, air pressure for spray: 0.3 MPa, air supply temperature: 80° C.) to thus give coated granules (average particle size: 117 μm).

Furthermore, there were blended 2600 g of the resulting coated granules, 14640 g of PEARLITOL (ROQUETTE JAPAN Co., Ltd.), 540 g of Kollidon CL-F (BASF Japan Ltd.) and 40 g of CARPREX #67 (DSL Japan Co., Ltd.), together, followed by the addition, to the resulting blend, of 180 g of magnesium stearate (derived from vegetable) (Taihei Chemical Industry Co., Ltd.), the blending of these components and the subsequent forming of the resulting blend into tablets each having a weight of 180 mg and an imidafenacin content of 0.1 mg using a rotary tableting machine under a compressing pressure of 9 kN. The resulting tablets were inspected for the hardness and the time required for disintegration and as a result, they were found to be 5.6 kg (n=5) and 12 seconds (n=6), respectively.

Example 2

There were dissolved 20.0 g of imidafenacin and 10.0 g of Kollidon 90F (BASF Japan Ltd.) in a mixed liquid comprising 591 g of purified water and 1379 g of ethanol. Then, there was charged 4970 g of Starch 1500G (Colorcon Japan, LLC) into a fluidized bed granulator (FL-5, FREUND Industry Co., Ltd.) and the foregoing solution was then applied to (coated) the starch according to the top-spray technique (amount of liquid to be sprayed: 100 g/min, air pressure for spray: 0.3 MPa, air supply temperature: 70° C.) to thus give an imidafenacin-containing granulated product (average particle size: 124 μm; starch content: 99.4% by mass). Separately, there were dissolved 750 g of EUDRAGIT EPO (Rohm GmbH & Co. KG) and 375 g of magnesium stearate (derived from vegetable) (Taihei Chemical Industry Co., Ltd.) in a mixed liquid comprising 3412.5 g of purified water and 7962.5 g of ethanol. Then, there was charged 3750 g of the imidafenacin-containing granulated product prepared above into a fluidized bed granulator (FL-5, FREUND Industry Co., Ltd.) and the solution thus prepared was then applied to the granulated product according to the top-spray technique (amount of liquid to be sprayed: 100 g/min, air pressure for spray: 0.3 MPa, air supply temperature: 80° C.) to thus give coated granules (average particle size: 120 μm).

Furthermore, there were blended 3250 g of the resulting coated granules, 13990 g of PEARLITOL (ROQUETTE JAPAN Co., Ltd.), 540 g of Kollidon CL-F (BASF Japan Ltd.) and 40 g of CARPREX #67 (DSL Japan Co., Ltd.), together, followed by the addition, to the resulting blend, of 180 g of magnesium stearate (derived from vegetable) (Taihei Chemical Industry Co., Ltd.), the subsequent blending of these components and the forming of the resulting blend into tablets each having a weight of 180 mg and an imidafenacin content of 0.1 mg using a rotary tableting machine under a compressing pressure of 9 kN. The resulting tablets were inspected for the hardness and the time required for disintegration and as a result, they were found to be 4.9 kg (n=5) and 10 seconds (n=6), respectively.

Example 3

There were dissolved 16.7 g of imidafenacin and 8.3 g of Kollidon 90F (BASF Japan Ltd.) in a mixed liquid comprising 483.5 g of purified water and 1151.5 g of ethanol. Then, there was charged 4975 g of Starch 1500G (Colorcon Japan, LLC) into a fluidized bed granulator (FL-5, FREUND Industry Co., Ltd.) and the foregoing solution was then applied to (coated) the starch according to the top-spray technique (amount of liquid to be sprayed: 100 g/min, air pressure for spray: 0.3 MPa, air supply temperature: 70° C.) to thus give an imidafenacin-containing granulated product (average particle size: 119 μm; starch content: 99.5% by mass). Separately, there were dissolved 750 g of EUDRAGIT EPO (Rohm GmbH & Co. KG) and 375 g of magnesium stearate (derived from vegetable) (Taihei Chemical Industry Co., Ltd.) in a mixed liquid comprising 3412.5 g of purified water and 7962.5 g of ethanol. Then, there was charged 3750 g of the imidafenacin-containing granulated product prepared above into a fluidized bed granulator (FL-5, FREUND Industry Co., Ltd.) and the solution thus prepared was then applied to the granulated product according to the top-spray technique (amount of liquid to be sprayed: 100 g/min, air pressure for spray: 0.3 MPa, air supply temperature: 80° C.) to thus give coated granules (average particle size: 115 μm).

Furthermore, there were blended 3900 g of the resulting coated granules, 13340 g of PEARLITOL (ROQUETTE JAPAN Co., Ltd.), 540 g of Kollidon CL-F (BASF Japan Ltd.) and 40 g of CARPREX #67 (DSL Japan Co., Ltd.), together, followed by the addition, to the resulting blend, of 180 g of magnesium stearate (derived from vegetable) (Taihei Chemical Industry Co., Ltd.), the subsequent blending of these components and the forming of the resulting blend into tablets each having a weight of 180 mg and an imidafenacin content of 0.1 mg using a rotary tableting machine under a compressing pressure of 9 kN. The resulting tablets were inspected for the hardness and the time required for disintegration and as a result, they were found to be 5.2 kg (n=5) and 16 seconds (n=6), respectively.

Example 4

There were dissolved 25.0 g of imidafenacin and 12.5 g of Kollidon 90F (BASF Japan Ltd.) in a mixed liquid comprising 738.75 g of purified water and 1723.75 g of ethanol. Then, there were charged 2500 g of Starch 1500G (Colorcon Japan, LLC) and 2462.5 g of CEOLUS PH-301 (ASAHIKASEI Chemicals Co., Ltd.) into a fluidized bed granulator (FL-5, FREUND Industry Co., Ltd.) and the foregoing solution was then applied to (coated) the starch and cellulose mixture according to the top-spray technique (amount of liquid to be sprayed: 100 g/min, air pressure for spray: 0.3 MPa, air supply temperature: 70° C.) to thus give an imidafenacin-containing granulated product (average particle size: 85 μm; starch content: 50% by mass). Separately, there were dissolved 750 g of EUDRAGIT EPO (Rohm GmbH & Co. KG) and 375 g of magnesium stearate (derived from vegetable) (Taihei Chemical Industry Co., Ltd.) in a mixed liquid comprising 3412.5 g of purified water and 7962.5 g of ethanol. Then, there was charged 3750 g of the imidafenacin-containing granulated product prepared above into a fluidized bed granulator (FL-5, FREUND Industry Co., Ltd.) and the solution thus prepared was then applied to the granulated product according to the top-spray technique (amount of liquid to be sprayed: 100 g/min, air pressure for spray: 0.3 MPa, air supply temperature: 80° C.) to thus give coated granules (average particle size: 118 μm).

Furthermore, there were blended 2600 g of the resulting coated granules, 14640 g of PEARLITOL (ROQUETTE JAPAN Co., Ltd.), 540 g of Kollidon CL-F (BASF Japan Ltd.) and 40 g of CARPREX #67 (DSL Japan Co., Ltd.), together, followed by the addition, to the resulting blend, of 180 g of magnesium stearate (derived from vegetable) (Taihei Chemical Industry Co., Ltd.), the subsequent blending of these components and the forming of the resulting blend into tablets each having a weight of 180 mg and an imidafenacin content of 0.1 mg using a rotary tableting machine under a compressing pressure of 7.7 kN. The resulting tablets were inspected for the hardness and the time required for disintegration and as a result, they were found to be 5.2 kg (n=5) and 12 seconds (n=6), respectively Example 5

There were dissolved 20.0 g of imidafenacin and 10.0 g of Kollidon 90F (BASF Japan Ltd.) in a mixed liquid comprising 591 g of purified water and 1379 g of ethanol. Then, there were charged 2500 g of Starch 1500G (Colorcon Japan, LLC) and 2470 g of CEOLUS PH-301 (ASAHIKASEI Chemicals Co., Ltd.) into a fluidized bed granulator (FL-5, FREUND Industry Co., Ltd.) and the foregoing solution was then applied to (coated) the starch and cellulose mixture according to the top-spray technique (amount of liquid to be sprayed: 120 g/min, air pressure for spray: 0.3 MPa, air supply temperature: 70° C.) to thus give an imidafenacin-containing granulated product (average particle size: 80 μm; starch content: 50% by mass). Separately, there were dissolved 750 g of EUDRAGIT EPO (Rohm GmbH & Co. KG) and 375 g of magnesium stearate (derived from vegetable) (Taihei Chemical Industry Co., Ltd.) in a mixed liquid comprising 3412.5 g of purified water and 7962.5 g of ethanol. Then, there was charged 3750 g of the imidafenacin-containing granulated product prepared above into a fluidized bed granulator (FL-5, FREUND Industry Co., Ltd.) and the solution thus prepared was then applied to the granulated product according to the top-spray technique (amount of liquid to be sprayed: 100 g/min, air pressure for spray: 0.3 MPa, air supply temperature: 80° C.) to thus give coated granules (average particle size: 123 μm).

Furthermore, there were blended 3250 g of the resulting coated granules, 13990 g of PEARLITOL (ROQUETTE JAPAN Co., Ltd.), 540 g of Kollidon CL-F (BASF Japan Ltd.) and 40 g of CARPREX #67 (DSL Japan Co., Ltd.), together, followed by the addition, to the resulting blend, of 180 g of magnesium stearate (derived from vegetable) (Taihei Chemical Industry Co., Ltd.), the subsequent blending of these components and the forming of the resulting blend into tablets each having a weight of 180 mg and an imidafenacin content of 0.1 mg using a rotary tableting machine under a compressing pressure of 7.2 kN. The resulting tablets were inspected for the hardness and the time required for disintegration and as a result, they were found to be 5.5 kg (n=5) and 15 seconds (n=6), respectively.

Example 6

There were dissolved 16.7 g of imidafenacin and 8.3 g of Kollidon 90F (BASF Japan Ltd.) in a mixed liquid comprising 483.5 g of purified water and 1151.5 g of ethanol. Then, there were charged 2500 g of Starch 1500G (Colorcon Japan, LLC) and 2475 g of CEOLUS PH-301 (ASAHIKASEI Chemicals Co., Ltd.) into a fluidized bed granulator (FL-5, FREUND Industry Co., Ltd.) and the foregoing solution was then applied to (coated) the starch and cellulose mixture according to the top-spray technique (amount of liquid to be sprayed: 160 g/min, air pressure for spray: 0.3 MPa, air supply temperature: 70° C.) to thus give an imidafenacin-containing granulated product (average particle size: 87 μm; starch content: 50% by mass). Separately, there were dissolved 750 g of EUDRAGIT EPO (Rohm GmbH & Co. KG) and 375 g of magnesium stearate (derived from vegetable) (Taihei Chemical Industry Co., Ltd.) in a mixed liquid comprising 3412.5 g of purified water and 7962.5 g of ethanol. Then, there was charged 3750 g of the foregoing imidafenacin-containing granulated product into a fluidized bed granulator (FL-5, FREUND Industry Co., Ltd.) and the solution thus prepared was then applied to the granulated product according to the top-spray technique (amount of liquid to be sprayed: 100 g/min, air pressure for spray: 0.3 MPa, air supply temperature: 80° C.) to thus give coated granules (average particle size: 99 μm).

Furthermore, there were blended 3900 g of the resulting coated granules, 13340 g of PEARLITOL (ROQUETTE JAPAN Co., Ltd.), 540 g of Kollidon CL-F (BASF Japan Ltd.) and 40 g of CARPREX #67 (DSL Japan Co., Ltd.), together, followed by the addition, to the resulting blend, of 180 g of magnesium stearate (derived from vegetable) (Taihei Chemical Industry Co., Ltd.), the subsequent blending of these components and the forming of the resulting blend into tablets each having a weight of 180 mg and an imidafenacin content of 0.1 mg using a rotary tableting machine under a compressing pressure of 7.2 kN. The resulting tablets were inspected for the hardness and the time required for disintegration and as a result, they were found to be 5.4 kg (n=5) and 12 seconds (n=6), respectively.

Example 7

There were dissolved 25.0 g of imidafenacin, 125 g of EUDRAGIT EPO (Rohm GmbH & Co. KG) and 62.5 g of magnesium stearate (derived from vegetable) (Taihei Chemical Industry Co., Ltd.) in a mixed liquid comprising 915 g of purified water and 1372.5 g of ethanol. Then, there was charged 4787.5 g of Starch 1500G (Colorcon Japan, LLC) into a fluidized bed granulator (FL-5, FREUND Industry Co., Ltd.) and the foregoing solution was then applied to (coated) the starch according to the top-spray technique (amount of liquid to be sprayed: 100 g/min, air pressure for spray: 0.3 MPa, air supply temperature: 70° C.) to thus give an imidafenacin-containing granulated product (average particle size: 115 μm; starch content: 95.75% by mass). Separately, there were dissolved 940 g of EUDRAGIT EPO (Rohm GmbH & Co. KG) and 470 g of magnesium stearate (derived from vegetable) (Taihei Chemical Industry Co., Ltd.) in a mixed liquid comprising 5702.8 g of purified water and 8554.2 g of ethanol. Then, there was charged 4700 g of the foregoing imidafenacin-containing granulated product into a fluidized bed granulator (FL-5, FREUND Industry Co., Ltd.) and the solution thus prepared was then applied to the granulated product according to the top-spray technique (amount of liquid to be sprayed: 100 g/min, air pressure for spray: 0.3 MPa, air supply temperature: 80° C.) to thus give coated granules (average particle size: 123 μm).

Furthermore, there were blended 2600 g of the resulting coated granules, 14640 g of PEARLITOL (ROQUETTE JAPAN Co., Ltd.), 540 g of Kollidon CL-F (BASF Japan Ltd.) and 40 g of CARPREX #67 (DSL Japan Co., Ltd.), together, followed by the addition, to the resulting blend, of 180 g of magnesium stearate (derived from vegetable) (Taihei Chemical Industry Co., Ltd.), the subsequent blending of these components and the forming of the resulting blend into tablets each having a weight of 180 mg and an imidafenacin content of 0.1 mg using a rotary tableting machine under a compressing pressure of 8.6 kN. The resulting tablets were inspected for the hardness and the time required for disintegration and as a result, they were found to be 5.6 kg (n=5) and 12 seconds (n=6), respectively.

Comparative Example 1

There were dissolved 4.0 g of imidafenacin and 4 g of Kollidon 90F (BASF Japan Ltd.) in a mixed liquid comprising 196 g of purified water and 196 g of ethanol. There was charged 392 g of PEARLITOL (ROQUETTE JAPAN Co., Ltd.) into a tumbling fluidized bed granulator (NQ-160, Dalton Company) and the solution prepared above was then applied to (coated) the sugar alcohol according to the top-spray technique (amount of liquid to be sprayed: 15 g/min, air pressure for spray: 0.1 MPa, air supply temperature: 50° C.) to thus give an imidafenacin-containing granulated product.

Moreover, there were blended, together, 25 g of this imidafenacin-containing granulated product, 374.5 g of PEARLITOL (ROQUETTE JAPAN Co., Ltd.), 45 g of POLYPLASDONE XL-10 (ISP Company) and 1 g of CARPREX #67 (DSL Japan Co., Ltd.), followed by the addition, to the resulting blend, of 4.5 g of magnesium stearate (derived from vegetable) (Taihei Chemical Industry Co., Ltd.), the subsequent blending of these components and the forming of the resulting blend into tablets each having a weight of 180 mg and an imidafenacin content of 0.1 mg using a rotary tableting machine under a compressing pressure of 1,000 kg. The resulting tablets were inspected for the hardness and as a result, it was found to be 7.2 kg (n=5).

Comparative Example 2

There were dissolved 4.0 g of imidafenacin and 40 g of POLYPLASDONE XL-10 (ISP Company) in a mixed liquid comprising 178 g of purified water and 178 g of ethanol. Then, there was charged 356 g of Starch 1500G (Colorcon Japan, LLC) into a tumbling fluidized bed granulator (NQ-160, Dalton Company) and the solution prepared above was then applied to (coated) the starch according to the top-spray technique (amount of liquid to be sprayed: 15 g/min, air pressure for spray: 0.1 MPa, air supply temperature: 50° C.) to thus give an imidafenacin-containing granulated product (starch content: 89% by mass).

Moreover, there were blended, together, 25 g of this imidafenacin-containing granulated product, 374.5 g of PEARLITOL (ROQUETTE JAPAN), 45 g of POLYPLASDONE XL-10 (ISP Company) and 1 g of CARPREX #67 (DSL Japan Co., Ltd.), followed by the addition, to the resulting blend, of 4.5 g of magnesium stearate (derived from vegetable) (Taihei Chemical Industry Co., Ltd.), the subsequent blending of these components and the forming of the resulting blend into tablets each having a weight of 180 mg and an imidafenacin content of 0.1 mg using a rotary tableting machine under a compressing pressure of 850 kg. The resulting tablets were inspected for the hardness and as a result, it was found to be 4.8 kg (n=5).

Test Example 1

The pharmaceutical preparations prepared in the foregoing Examples 1 to 6 were subjected to a test for evaluating the photostability thereof. Each sample was irradiated with light rays emitted from D65 lamp at an illuminance of 4500 Lx over about 12 days. In this respect, the photostability was evaluated on the basis of the amount of degradation products formed during the term. The results thus obtained are summarized in the following Table 1. Incidentally, the quantitative analysis of the degradation products was carried out according to the liquid chromatography technique (HPLC technique). In this connection, the higher the numerical value represented by percentage (%), the lower the photostability of the sample.

HPLC Technique:
Column Used: Octadecylsilanized silica gel (average particle size: 5 μm; 4.6 mm (inner diameter)×250 mm (length)) (GL Science Co., Ltd. under the trade name of Inertsil ODS-3,);
Liquid A: Diethylamine was added to a diluted phosphoric acid (1→200) and the pH value thereof was controlled to 6.0;
Liquid B: Acetonitrile of liquid chromatography grade;
Liquid C: Methanol of liquid chromatography grade;
Carrier Liquid: The concentration gradient was controlled by changing the mixing ratio of the liquid A, liquid B and liquid C; Detector: UV;
Wavelength Used for Measurement: 220 nm.

TABLE 1

| Sample | Before Light Irradiation | | After Light Irradiation | |
| --- | --- | --- | --- | --- |
| | Indiv. (max.), % | Total (%) | Indiv. (max.), % | Total (%) |
| Ex. 1 | 0.15 | 0.3 | 0.15 | 0.5 |
| Ex. 2 | 0.09 | 0.2 | 0.23 | 0.7 |
| Ex. 3 | 0.12 | 0.2 | 0.26 | 0.9 |
| Ex. 4 | 0.12 | 0.2 | 0.27 | 1.2 |
| Ex. 5 | 0.10 | 0.3 | 0.63 | 1.9 |
| Ex. 6 | 0.13 | 0.3 | 0.97 | 2.6 |
| Comp. Ex. 1 | ND | ND | 3.19 | 6.0 |
| Comp. Ex. 1 | 0.12 | 0.20 | 2.97 | 6.0 |

Example 8

There were dissolved 4.0 g of imidafenacin and 2 g of Kollidon 90F (BASF Japan Ltd.) in a mixed liquid comprising 157.6 g of purified water and 236.4 g of ethanol. Then, there was charged 794 g of Starch 1500G (Colorcon Japan, LLC) into a tumbling fluidized bed granulator (NQ-160, Dalton Co., Ltd.) and the foregoing solution was then applied to (coated) the starch according to the top-spray technique (amount of liquid to be sprayed: 18 g/min, air pressure for spray: 0.1 MPa, air supply temperature: 70° C.) to thus give an imidafenacin-containing granulated product (average particle size: 127 μm; starch content: 99.25% by mass). Separately, there were dissolved 60 g of EUDRAGIT EPO (Rohm GmbH & Co. KG) and 30 g of magnesium stearate (derived from vegetable) (Taihei Chemical Industry Co., Ltd.) in a mixed liquid comprising 364 g of purified water and 546 g of ethanol. Then, there was charged 300 g of the foregoing imidafenacin-containing granulated product into a tumbling fluidized bed granulator (NQ-160, Dalton Co., Ltd.) and the solution thus prepared was then applied to the granulated product according to the side-spray technique (amount of liquid to be sprayed: 20 g/min, air pressure for spray: 0.15 MPa, air supply temperature: 70° C.) to thus give coated granules.

Furthermore, there were blended 78.0 g of the resulting coated granules, 439.2 g of PEARLITOL (ROQUETTE JAPAN Co., Ltd.), 16.2 g of Kollidon CL-F (BASF Japan Ltd.) and 1.2 g of CARPREX #67 (DSL Japan Co., Ltd.), together, followed by the addition, to the resulting blend, of 5.4 g of magnesium stearate (derived from vegetable) (Taihei Chemical Industry Co., Ltd.), the subsequent blending of these components and the forming of the resulting blend into tablets each having a weight of 180 mg and an imidafenacin content of 0.1 mg using a rotary tableting machine under a compressing pressure of 800 kg. The resulting tablets were inspected for the hardness and as a result, it was found to be 5.2 kg (n=5).

Example 9

There were dissolved 4.0 g of imidafenacin and 2 g of Kollidon 90F (BASF Japan Ltd.) in a mixed liquid comprising 157.6 g of purified water and 236.4 g of ethanol. Then, there was charged 794 g of Starch 1500G (Colorcon Japan, LLC) into a tumbling fluidized bed granulator (NQ-160, Dalton Co., Ltd.) and the foregoing solution was then applied to (coated) the starch according to the top-spray technique (amount of liquid to be sprayed: 18 g/min, air pressure for spray: 0.1 MPa, air supply temperature: 70° C.) to thus give an imidafenacin-containing granulated product (average particle size: 128 µm; starch content: 99.25% by mass). Separately, there were dissolved 60 g of AEA (Sankyo LifeTech Co., Ltd.) and 30 g of magnesium stearate (derived from vegetable) (Taihei Chemical Industry Co., Ltd.) in a mixed liquid comprising 91 g of purified water and 819 g of ethanol. Then, there was charged 300 g of the imidafenacin-containing granulated product prepared above into a tumbling fluidized bed granulator (NQ-160, Dalton Co., Ltd.) and the solution thus prepared was then applied to the granulated product according to the side-spray technique (amount of liquid to be sprayed: 20 g/min, air pressure for spray: 0.2 MPa, air supply temperature: 60° C.) to thus give coated granules.

Furthermore, there were blended 78.0 g of the resulting coated granules, 439.2 g of PEARLITOL (ROQUETTE JAPAN Co., Ltd.), 16.2 g of Kollidon CL-F (BASF Japan Ltd.) and 1.2 g of CARPREX #67 (DSL Japan Co., Ltd.), together, followed by the addition, to the resulting blend, of 5.4 g of magnesium stearate (derived from vegetable) (Taihei Chemical Industry Co., Ltd.), the subsequent mixing of these components and the forming of the resulting blend into tablets each having a weight of 180 mg and an imidafenacin content of 0.1 mg using a rotary tableting machine under a compressing pressure of 800 kg. The resulting tablets were inspected for the hardness and as a result, it was found to be 4.8 kg (n=5).

Example 10

There were dissolved 4.0 g of imidafenacin and 2 g of Kollidon 90F (BASF Japan Ltd.) in a mixed liquid comprising 157.6 g of purified water and 236.4 g of ethanol. Then, there was charged 794 g of Starch 1500G (Colorcon Japan, LLC) into a tumbling fluidized bed granulator (NQ-160, Dalton Co., Ltd.) and the foregoing solution was then applied to (coated) the starch according to the top-spray technique (amount of liquid to be sprayed: 18 g/min, air pressure for spray: 0.1 MPa, air supply temperature: 70° C.) to thus give an imidafenacin-containing granulated product (starch content: 99.25% by mass). Separately, there were dissolved 60 g of EUDRAGIT L100-55 (Rohm GmbH & Co. KG) and 30 g of magnesium stearate (derived from vegetable) (Taihei Chemical Industry Co., Ltd.) in a mixed liquid comprising 91 g of purified water and 819 g of ethanol. Then, there was charged 300 g of the imidafenacin-containing granulated product prepared above into a tumbling fluidized bed granulator (NQ-160, Dalton Co., Ltd.) and the solution thus prepared was then applied to the granulated product according to the side-spray technique (amount of liquid to be sprayed: 10 g/min, air pressure for spray: 0.15 MPa, air supply temperature: 50° C.) to thus give coated granules.

Furthermore, there were blended 78.0 g of the resulting coated granules, 439.2 g of PEARLITOL (ROQUETTE JAPAN Co., Ltd.), 16.2 g of Kollidon CL-F (BASF Japan Ltd.) and 1.2 g of CARPREX #67 (DSL Japan Co., Ltd.), together, followed by the addition, to the resulting blend, of 5.4 g of magnesium stearate (derived from vegetable) (Taihei Chemical Industry Co., Ltd.), the subsequent mixing of these components and the forming of the resulting blend into tablets each having a weight of 180 mg and an imidafenacin content of 0.1 mg using a rotary tableting machine under a compressing pressure of 830 kg. The resulting tablets were inspected for the hardness and as a result, it was found to be 5.5 kg (n=5).

Example 11

There were dissolved 4.0 g of imidafenacin and 2 g of Kollidon 90F (BASF Japan Ltd.) in a mixed liquid comprising 157.6 g of purified water and 236.4 g of ethanol. Then, there was charged 794 g of Starch 1500G (Colorcon Japan, LLC) into a tumbling fluidized bed granulator (NQ-160, Dalton Co., Ltd.) and the foregoing solution was then applied to (coated) the starch according to the top-spray technique (amount of liquid to be sprayed: 18 g/min, air pressure for spray: 0.1 MPa, air supply temperature: 70° C.) to thus give an imidafenacin-containing granulated product (average particle size: 128 µm; starch content: 99.25% by mass). Separately, there were dissolved 60 g of EUDRAGIT RSPO (Rohm GmbH & Co. KG) and 30 g of magnesium stearate (derived from vegetable) (Taihei Chemical Industry Co., Ltd.) in a mixed liquid comprising 91 g of purified water and 819 g of ethanol. Then, there was charged 300 g of the imidafenacin-containing granulated product prepared above into a tumbling fluidized bed granulator (NQ-160, Dalton Co., Ltd.) and the solution thus prepared was then applied to the granulated product according to the side-spray technique (amount of liquid to be sprayed: 20 g/min, air pressure for spray: 0.15 MPa, air supply temperature: 60° C.) to thus give coated granules.

Furthermore, there were blended 78.0 g of the resulting coated granules, 439.2 g of PEARLITOL (ROQUETTE JAPAN Co., Ltd.), 16.2 g of Kollidon CL-F (BASF Japan Ltd.) and 1.2 g of CARPREX #67 (DSL Japan Co., Ltd.), together, followed by the addition, to the resulting blend, of 5.4 g of magnesium stearate (derived from vegetable) (Taihei Chemical Industry Co., Ltd.), the subsequent mixing of these components and the forming of the resulting blend into tablets each having a weight of 180 mg and an imidafenacin content of 0.1 mg using a rotary tableting machine under a compressing pressure of 780 kg. The resulting tablets were inspected for the hardness and as a result, it was found to be 4.8 kg (n=5).

Example 12

There were dissolved 4.0 g of imidafenacin and 2 g of Kollidon 90F (BASF Japan Ltd.) in a mixed liquid comprising 157.6 g of purified water and 236.4 g of ethanol. Then, there was charged 794 g of Starch 1500G (Colorcon Japan, LLC) into a tumbling fluidized bed granulator (NQ-160, Dalton Co., Ltd.) and the foregoing solution was then applied to (coated) the starch according to the top-spray technique (amount of liquid to be sprayed: 18 g/min, air pressure for spray: 0.1 MPa, air supply temperature: 70° C.) to thus give an imidafenacin-containing granulated product (average particle size: 127 μm; starch content: 99.25% by mass). Separately, there were dissolved 60 g of Kollidon 25 (BASF Japan Ltd.) and 30 g of magnesium stearate (derived from vegetable) (Taihei Chemical Industry Co., Ltd.) in a mixed liquid comprising 364 g of purified water and 546 g of ethanol. Then, there was charged 300 g of the imidafenacin-containing granulated product prepared above into a tumbling fluidized bed granulator (NQ-160, Dalton Co., Ltd.) and the solution thus prepared was then applied to the granulated product according to the side-spray technique (amount of liquid to be sprayed: 15 g/min, air pressure for spray: 0.15 MPa, air supply temperature: 70° C.) to thus give coated granules.

Furthermore, there were blended 78.0 g of the resulting coated granules, 439.2 g of PEARLITOL (ROQUETTE JAPAN Co., Ltd.), 16.2 g of Kollidon CL-F (BASF Japan Ltd.) and 1.2 g of CARPREX #67 (DSL Japan Co., Ltd.), together, followed by the addition, to the resulting blend, of 5.4 g of magnesium stearate (derived from vegetable) (Taihei Chemical Industry Co., Ltd.), the subsequent mixing of these components and the forming of the resulting blend into tablets each having a weight of 180 mg and an imidafenacin content of 0.1 mg using a rotary tableting machine under a compressing pressure of 820 kg. The resulting tablets were inspected for the hardness and as a result, it was found to be 4.9 kg (n=5).

Comparative Example 3

There were dissolved 4.0 g of imidafenacin and 2 g of Kollidon 90F (BASF Japan Ltd.) in a mixed liquid comprising 157.6 g of purified water and 236.4 g of ethanol. Then, there was charged 794 g of Starch 1500G (Colorcon Japan, LLC) into a tumbling fluidized bed granulator (NQ-160, Dalton Co., Ltd.) and the foregoing solution was then applied to (coated) the starch according to the top-spray technique (amount of liquid to be sprayed: 18 g/min, air pressure for spray: 0.1 MPa, air supply temperature: 70° C.) to thus give an imidafenacin-containing granulated product (average particle size: 129 μm; starch content: 99.25% by mass). Furthermore, there were blended 60.0 g of the resulting imidafenacin-containing granulated product, 457.2 g of PEARLITOL (ROQUETTE JAPAN Co., Ltd.), 16.2 g of Kollidon CL-F (BASF Japan Ltd.) and 1.2 g of CARPREX #67 (DSL Japan Co., Ltd.), together, followed by the addition, to the resulting blend, of 5.4 g of magnesium stearate (derived from vegetable) (Taihei Chemical Industry Co., Ltd.), the subsequent mixing of these components and the forming of the resulting blend into tablets each having a weight of 180 mg and an imidafenacin content of 0.1 mg using a rotary tableting machine under a compressing pressure of 790 kg. The resulting tablets were inspected for the hardness and as a result, it was found to be 4.9 kg (n=5).

Comparative Example 4

There were dissolved 4.0 g of imidafenacin and 2 g of Kollidon 90F (BASF Japan Ltd.) in a mixed liquid comprising 157.6 g of purified water and 236.4 g of ethanol. Then, there was charged 794 g of Starch 1500G (Colorcon Japan, LLC) into a tumbling fluidized bed granulator (NQ-160, Dalton Co., Ltd.) and the foregoing solution was then applied to (coated) the starch according to the top-spray technique (amount of liquid to be sprayed: 18 g/min, air pressure for spray: 0.1 MPa, air supply temperature: 70° C.) to thus give an imidafenacin-containing granulated product (average particle size: 130 μm; starch content: 99.25% by mass). Separately, there were dissolved 60 g of ETHOCEL 7 Premium (Nissin Chemical Industry Co., Ltd.) and 30 g of magnesium stearate (derived from vegetable) (Taihei Chemical Industry Co., Ltd.) in a mixed liquid comprising 91 g of purified water and 819 g of ethanol. Then, there was charged 300 g of the imidafenacin-containing granulated product prepared above into a tumbling fluidized bed granulator (NQ-160, Dalton Co., Ltd.) and the solution thus prepared was then applied to the granulated product according to the side-spray technique (amount of liquid to be sprayed: 20 g/min, air pressure for spray: 0.15 MPa, air supply temperature: 60° C.) to thus give coated granules.

Furthermore, there were blended 78.0 g of the resulting coated granules, 439.2 g of PEARLITOL (ROQUETTE JAPAN Co., Ltd.), 16.2 g of Kollidon CL-F (BASF Japan Ltd.) and 1.2 g of CARPREX #67 (DSL Japan Co., Ltd.), together, followed by the addition, to the resulting blend, of 5.4 g of magnesium stearate (derived from vegetable) (Taihei Chemical Industry Co., Ltd.), the subsequent mixing of these components and the forming of the resulting blend into tablets each having a weight of 180 mg and an imidafenacin content of 0.1 mg using a rotary tableting machine under a compressing pressure of 830 kg. The resulting tablets were inspected for the hardness and as a result, it was found to be 5.5 kg (n=5).

Comparative Example 5

There were dissolved 4.0 g of imidafenacin and 2 g of Kollidon 90F (BASF Japan Ltd.) in a mixed liquid comprising 157.6 g of purified water and 236.4 g of ethanol. Then, there was charged 794 g of Starch 1500G (Colorcon Japan, LLC) into a tumbling fluidized bed granulator (NQ-160, Dalton Co., Ltd.) and the foregoing solution was then applied to (coated) the starch according to the top-spray technique (amount of liquid to be sprayed: 18 g/min, air pressure for spray: 0.1 MPa, air supply temperature: 70° C.) to thus give an imidafenacin-containing granulated product (average particle size: 130 μm; starch content: 99.25% by mass). Separately, there were dissolved 60 g of TC-5RW (Shin-Etsu Chemical Co., Ltd.) and 30 g of magnesium stearate (derived from vegetable) (Taihei Chemical Industry Co., Ltd.) in a mixed liquid comprising 364 g of purified water and 546 g of ethanol. Then, there was charged 300 g of the imidafenacin-containing granulated product prepared above into a tumbling fluidized bed granulator (NQ-160, Dalton Co., Ltd.) and the solution thus prepared was then applied to the granulated product according to the side-spray technique (amount of liquid to be sprayed: 15 g/min, air pressure for spray: 0.15 MPa, air supply temperature: 70° C.) to thus give coated granules.

Furthermore, there were blended 78.0 g of the resulting coated granules, 439.2 g of PEARLITOL (ROQUETTE JAPAN Co., Ltd.), 16.2 g of Kollidon CL-F (BASF Japan Ltd.) and 1.2 g of CARPREX #67 (DSL Japan Co., Ltd.), together, followed by the addition, to the resulting blend, of 5.4 g of magnesium stearate (derived from vegetable) (Taihei Chemical Industry Co., Ltd.), the subsequent mixing of these components and the forming of the resulting blend into tablets each having a weight of 180 mg and an imidafenacin content of 0.1 mg using a rotary tableting machine under a compressing pressure of 800 kg. The resulting tablets were inspected for the hardness and as a result, it was found to be 4.4 kg (n=5).

Test Example 2

The pharmaceutical preparations prepared in the foregoing Examples 8 to 12 and Comparative Examples 3 to 5 were subjected to a test for evaluating the photostability thereof. Each sample was irradiated with light rays emitted from D65 lamp at an illuminance of 2000 to 4500 Lx over about 18 days. In this respect, the photostability was evaluated on the basis of the amount of degradation products formed during the term. The results thus obtained are summarized in the following Table 2. Incidentally, the quantitative analysis of the degradation products was carried out according to the liquid chromatography technique (HPLC technique).

HPLC Technique:
Column Used: Octadecylsilanized silica gel (average particle size: 5 μm; 4.6 mm (inner diameter)×150 mm (length)) (GL Science Co., Ltd. under the trade Name of Inertsil ODS-3);
Liquid A: Sodium octane sulfonate (1.08 g) was dissolved in a diluted phosphoric acid (1→1000), followed by the adjustment of the final volume to 1000 mL;
Liquid B: Acetonitrile of liquid chromatography grade;
Carrier Liquid: The concentration gradient was controlled by changing the mixing ratio of the liquid A to the liquid B;
Detector: UV;
Wavelength Used for Measurement: 220 nm.

TABLE 2

| Sample | Before Light Irradiation | | After Light Irradiation | |
|---|---|---|---|---|
| | Indiv. (max.), % | Total (%) | Indiv. (max.), % | Total (%) |
| Ex. 8 | 0.08 | 0.1 | 0.19 | 0.5 |
| Ex. 9 | ND | — | 0.3 | 0.7 |
| Ex. 10 | 0.03 | 0.1 | 1.16 | 2.6 |
| Ex. 11 | 0.06 | 0.1 | 0.66 | 1.9 |
| Ex. 12 | 0.05 | 0.1 | 1.49 | 3 |
| Comp. Ex. 3 | 0.03 | 0.1 | 7.65 | 13.7 |
| Comp. Ex. 4 | 0.35 | 0.5 | 8.69 | 21.1 |
| Comp. Ex. 5 | 0.04 | 0.1 | 3.24 | 7.1 |

Test Example 3

The pharmaceutical preparations prepared in Examples 1 to 6 were tested on the content uniformity.

Test for Evaluating the Content Uniformity:

The candidate pharmaceutical preparations (10 tablets each) were taken and the content of imidafenacin was evaluated according to the high performance liquid chromatography (HPLC) technique. The content of the principal ingredient (effective component) (the rate (%) of the principal ingredient relative to the indicated quantity (100%)) and the average value thereof were calculated and the standard deviation (see the equation (1) given below) and the acceptance value of the content uniformity (see the equation (2) given below) were determined.

[Numerical Formula 1]

$$S = \sqrt{\frac{\sum_{i=1}^{n}(X_i - A)^2}{n-1}} \quad (1)$$

In the formula (1), S means the standard deviation; n represents the total number (10) of each sample tested; X represents the content of the main ingredient (the rate (%) of the main ingredient relative to the indicated quantity (100%)) present in each individual sample tested; and A represents the average of the measured values (contents) $X_1$ to $X_n$.

$$\text{Acceptance value} = |100 - A| + S \times 2.2 \quad (2)$$

In this formula, A and S are the same as those defined above in connection with the foregoing formula (1).

In addition, when "the acceptance value ranges from 0 to 15%" and "the standard deviation ranges from 0 to 3.5%", the amount of scatter in the measured values of the drug (effective component) contents present in the tablets prepared is quite small and accordingly, it would be recognized that the effective component never causes any segregation of the effective component between the tablets prepared and it would be said that "the drug content uniformity of the effective component is certainly insured among the resulting tablets". On the other hand, when "the acceptance value is beyond the range of from 0 to 15%" and "the standard deviation is also beyond the range of from 0 to 3.5%," the amount of scatter in the measured values of the drug (effective component) contents is quite large and accordingly, it would be recognized that the effective component surely causes the segregation of the effective component among the tablets and it would likewise be said that "the tablets each have a low drug content uniformity of the effective component in the resulting tablets." In this respect, the term "the appropriate range of the standard deviation" or "the standard deviation ranging from 0 to 3.5%" specified in the present invention means one of the numerical values, which are considered to be needed for the quality assurance and which would indicate the fact that a composition obtained certainly comprises a desired constant amount of an effective component.

HPLC Technique:
Column Used: Octadecylsilanized silica gel (average particle size: 3 μm; 4.6 mm (inner diameter)×50 mm (length)) (GL Science Co., Ltd. under the trade Name of Inertsil ODS-3);
Mobile Phase: Sodium 1-octane sulfonate (1.08 g) was dissolved in a diluted phosphoric acid (1→1000), followed by adjusting the final volume to 1000 mL. To 700 mL of this liquid, there was added 300 mL of acetonitrile of liquid chromatography grade;
Detector: UV;
Wavelength Used for Measurement: 220 nm.

TABLE 3

| Sample | Average Content (%) | Standard Deviation (σ) | Acceptance Value (%) |
|---|---|---|---|
| Ex. 1 | 104.7 | 1.7 | 8.4 |
| Ex. 2 | 103.6 | 0.9 | 5.6 |
| Ex. 3 | 104.0 | 0.8 | 5.8 |
| Ex. 4 | 102.7 | 1.2 | 5.3 |
| Ex. 5 | 104.6 | 1.4 | 7.7 |
| Ex. 6 | 104.3 | 1.2 | 6.9 |

The data listed in the foregoing Table 1 clearly indicate that, in respect of the pharmaceutical preparations prepared in Examples 1 to 6, the amount of the degradation products generated when the tablets prepared from the preparations are irradiated with light rays is reduced along with the increase of the concentration of imidafenacin present in the imidafenacin-containing granulated product. Moreover, when the results thus observed are compared between Example 1 and Example 4; between Example 2 and Example 5; and between Example 3 and Example 6, it is found that the greater the amount of starch present in the granulated product, the smaller the amount of the degradation products generated when the tablets prepared from the preparations are irradiated with light rays. With regard to the pharmaceutical preparations prepared in Examples 1 to 6, the total amount of the generated degradation products does not exceed 3% and the maximum amount of the generated individual degradation products does not exceed 1%. This clearly indicates that these pharmaceutical preparations would be stable to light. Contrary to this, the total amount of the generated degradation products exceeds 5% and the maximum amount of the generated individual degradation products surely exceeds 2% in the tablets prepared in Comparative Example 1 wherein the granulated product is prepared without using starch and the granulated product is not subjected to any coating treatment and in the tablets prepared in Comparative Example 2 wherein the granulated product is not subjected to any coating treatment.

Furthermore, in case of the tablets prepared in Examples 8 to 12 in which the granulated products are formed using starch and they are coated with a various kinds of non-cellulosic coating agents, the total amount of the degradation products does not exceed 3% and the tablets or the pharmaceutical preparations would thus be considered to be stable to light rays. However, the total amount of the degradation products surely exceeds 13%, in case of the tablets or the pharmaceutical preparation obtained in Comparative Example 3 in which the granulated product is not coated with any coating agent, and the total amount of the degradation products surely exceeds 7%, in case of the tablets or the pharmaceutical preparations obtained in Comparative Examples 4 and 5 in which the granulated product is coated with a cellulosic coating agent. Accordingly, the pharmaceutical preparations prepared in these Comparative Examples would show substantially reduced or impaired photostability.

In addition, it can be confirmed, on the basis of the data listed in the foregoing Table 3, that the pharmaceutical preparations prepared in Examples 1 to 6 clearly show excellent content uniformity since the standard deviations do not exceed 3.5 and the acceptance values do not exceed 15.0. Moreover, the results observed for the pharmaceutical preparations prepared in Examples 1 to 3 clearly indicate that the content uniformity is reduced as the imidafenacin concentration in the imidafenacin-containing granulated product increases.

INDUSTRIAL APPLICABILITY

The present invention permits the preparation of an imidafenacin-containing orally rapidly disintegrating tablet which is excellent in the photostability and the uniformity of content.

What is claimed is:

1. A method for preparing an orally rapidly disintegrating tablet comprising:
   granulating imidafenacin together with starch such that a granulated product comprising the imidafenacin having an imidafenacin concentration ranging from 0.001 to 3% by mass and the starch having a starch concentration ranging from 40 to 99.999% by mass is prepared;
   covering the granulated product with a non-cellulosic coating agent such that a coated granulated product comprising the granulated product and the non-cellulosic coating agent coating the granulated product is prepared;
   blending the coated granulated product with an excipient and a disintegrating agent such that a resulting mixture comprising the excipient, the disintegrating agent and the coated granulated product is prepared; and
   forming the resulting mixture into a tablet according to a compression molding technique.

2. The method of claim 1, wherein the non-cellulosic coating agent is an aminoalkyl methacrylate copolymer.

3. The method of claim 1, wherein the non-cellulosic coating agent is aminoalkyl methacrylate copolymer E.

4. The method of claim 1, wherein the non-cellulosic coating agent is a polyvinyl acetal diethylaminoacetate.

5. The method of claim 1, wherein the imidafenacin concentration of the granulated product has the imidafenacin concentration ranging from 0.2 to 0.6% by mass.

6. The method of claim 1, wherein the starch concentration of the granulated product has the starch concentration ranging from 60 to 99.999% by mass.

7. The method of claim 1, wherein the starch concentration of the granulated product has the starch concentration ranging from 70 to 99.999% by mass.

8. The method of claim 2, wherein the imidafenacin concentration of the granulated product has the imidafenacin concentration ranging from 0.2 to 0.6% by mass.

9. The method of claim 2, wherein the starch concentration of the granulated product has the starch concentration ranging from 60 to 99.999% by mass.

10. The method of claim 2, wherein the starch concentration of the granulated product has the starch concentration ranging from 70 to 99.999% by mass.

11. The method of claim 3, wherein the imidafenacin concentration of the granulated product has the imidafenacin concentration ranging from 0.2 to 0.6% by mass.

12. The method of claim 3, wherein the starch concentration of the granulated product has the starch concentration ranging from 60 to 99.999% by mass.

13. The method of claim 3, wherein the starch concentration of the granulated product has the starch concentration ranging from 70 to 99.999% by mass.

14. The method of claim 4, wherein the imidafenacin concentration of the granulated product has the imidafenacin concentration ranging from 0.2 to 0.6% by mass.

15. The method of claim 4, wherein the starch concentration of the granulated product has the starch concentration ranging from 60 to 99.999% by mass.

16. The method of claim 4, wherein the starch concentration of the granulated product has the starch concentration ranging from 70 to 99.999% by mass.

17. The method of claim 1, further comprising drying the granulated product.

18. The method of claim 1, wherein the non-cellulosic coating agent is povidone.

19. The method of claim 1, wherein the non-cellulosic coating agent is a methacrylic acid copolymer.

20. The method of claim 1, wherein the non-cellulosic coating agent is an ammonio-methacrylate copolymer.

* * * * *

UNITED STATES PATENT AND TRADEMARK OFFICE
CERTIFICATE OF CORRECTION

PATENT NO. : 8,722,133 B2  
APPLICATION NO. : 12/865632  
DATED : May 13, 2014  
INVENTOR(S) : Ishizaki et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 628 days.

Signed and Sealed this
Twenty-ninth Day of September, 2015

Michelle K. Lee
*Director of the United States Patent and Trademark Office*